(12) United States Patent
Freeman et al.

(10) Patent No.: US 7,825,104 B2
(45) Date of Patent: Nov. 2, 2010

(54) METHODS AND COMPOSITIONS FOR TREATING FUNGAL INFECTIONS

(75) Inventors: Amihay Freeman, Youth Village (IL); Rina Segal, Tel Mond (IL); Yael Dror, Tel Mond (IL)

(73) Assignee: Ramot at Tel Aviv University Ltd., Tel Aviv (IL)

( * ) Notice: Subject to any disclaimer, the term of this patent is extended or adjusted under 35 U.S.C. 154(b) by 1713 days.

(21) Appl. No.: 10/484,623

(22) PCT Filed: Jul. 23, 2002

(86) PCT No.: PCT/US02/23252

§ 371 (c)(1), (2), (4) Date: Jun. 15, 2004

(87) PCT Pub. No.: WO03/009689

PCT Pub. Date: Feb. 6, 2003

(65) Prior Publication Data

US 2004/0220146 A1 Nov. 4, 2004

Related U.S. Application Data

(60) Provisional application No. 60/306,857, filed on Jul. 23, 2001.

(51) Int. Cl.
| | |
|---|---|
| *A01N 55/08* | (2006.01) |
| *A01N 33/02* | (2006.01) |
| *A01N 35/00* | (2006.01) |
| *A61K 31/69* | (2006.01) |
| *A61K 31/135* | (2006.01) |
| *A61K 31/12* | (2006.01) |
| *A61K 31/11* | (2006.01) |

(52) U.S. Cl. .......... 514/64; 514/649; 514/650; 514/657; 514/678; 514/682; 514/693; 514/699; 514/700

(58) Field of Classification Search .......... 514/64, 514/649, 650, 657–700
See application file for complete search history.

(56) References Cited

U.S. PATENT DOCUMENTS

| | | | |
|---|---|---|---|
| 3,646,098 A * | 2/1972 | Cyba .......... | 558/291 |
| 6,075,014 A * | 6/2000 | Weston et al. .......... | 514/64 |
| 6,423,519 B1 | 7/2002 | Bergnes et al. | |
| 6,576,789 B1 * | 6/2003 | Haber et al. .......... | 562/7 |
| 2002/0165121 A1* | 11/2002 | Brehove .......... | 514/1 |

FOREIGN PATENT DOCUMENTS

| | | | |
|---|---|---|---|
| GB | 2281210 A | * | 8/1993 |
| WO | 95/05081 A1 | | 2/1995 |
| WO | WO 98/17253 | * | 4/1998 |

OTHER PUBLICATIONS

Yalinkilic et al. (J. Wood Science, 1998, 44: 152-157).*
Merriam-Webster's Collegiate Dictionary (Tenth Edition): p. 311, (1993).*
Liu et al, AGRICOLA Abstract 95:17644 of Forest Products Journal, Jun. 1994, vol. 44, pp. 46-48.
Beesley et al, "The Inhibition of Class C β-Lactamases by Boronic Acids," Biochem J. 1983, vol. 209, p. 229-233.
Kiener et al, "Reversible Inhibitors of Penicillinases," Biochem J. 1978, vol. 169, p. 197-204.
Haccius, B., "Cytochemical Studies on the Effects of Boric Acid and Phenylboric Acid on Various Oxidases and Dehydrogenases in Oospora lactis (Fres.) Sacc. (cf. Geotrichum candidum Link.)", Archives of Microbiology, 1967, vol. 58, 53-62.
Liu, X., "A Preliminary Report on the Wood Preservative Properties of Phenolboronic Acid", Forest Products Journal. Jun. 1994, vol. 44, No. 6, 46-48, Abstract.
Reiss, J., "Development of *Aspergillus parasiticus* and Formation of Aflatoxin B₁ Under the Influence of Conidiogenesis Affecting Compounds", Archives of Microbiology. Dec. 11, 1982, vol. 133, 236-238.
Yalinkilic, et al., "Boron Addition to Non- or Low-Formaldehyde Cross-Linking Reagents to Enhance Biological Resistance and Dimensional Stability of Wood", Holz als Roh- und Werkstoff. 1999, vol. 57, No. 5, 351-357, Abstract.
Yalinkilic, et al., "Enhancement of the Biological Resistance of Wood by Phenylboronic Acid Treatment", Journal of Wood Science. 1998, vol. 44, No. 2, 152-157, Abstract.
Haccius, B., "Cytochemical Studies on the Effects of Boric Acid and Phenylboric Acid on Various Oxidases and Dehydrogenases in Oospora lactis (Fres.) Sacc. (cf. Geotrichum candidum Link.)", Archives of Microbiology, 1967, vol. 58, 53-62, Abstract.

* cited by examiner

*Primary Examiner*—Johann R Richter
*Assistant Examiner*—Mei-Ping Chui
(74) *Attorney, Agent, or Firm*—Browdy and Neimark, PLLC

(57) ABSTRACT

Phenylboronic acid and water soluble derivatives thereof and related boronic acid compounds are used for treating fungal and bacterial infections.

21 Claims, 1 Drawing Sheet

METHODS AND COMPOSITIONS FOR TREATING FUNGAL INFECTIONS

FIELD OF THE INVENTION

The present invention relates to methods and compositions for treating fungal infections, and more particularly, dermatophytoses or onchomycosis of the fingernail and the toenail, as well as fungal infections in plants.

BACKGROUND OF THE INVENTION

Many fungal infections, or mycoses, of humans and animals affect only the outer layers of skin. Although these, infections may be sometimes difficult to cure, they are not considered dangerous. Most cutaneous infections are caused by the homogeneous group of keratinophilic fungi known as dermatophytes. The dermatophyte *Trichophyton rubrum* is the major cause of tinea pedis and onychomycosis. Fungal infections of the mucous membranes are caused primarily by *Candida albicans*, usually affecting the mouth and the vaginal and anal regions.

Fungal infections sometimes follow the use of antibiotics, which kill non-pathogenic as well as pathogenic bacteria, thereby providing a clear field for fungal invasion. Opportunistic fungal infection occurs when a fungus enters a compromised host, such as a patient suffering from AIDS.

Dermatophytoses of the fingernails and toenails, in contrast to those at other body sites, are particularly difficult to eradicate with drug treatment, particularly with topical treatment. This is the consequence of factors that are intrinsic to the nail such as the hard, protective nail plate, sequestration of pathogens between the nail bed and plate, and slow growth of the nail, as well as the relatively poor efficacy of the early pharmacologic agents.

"Onychomycosis" has traditionally referred to a non-dermatophytic infection of the nail. Onychomycosis is now used as a general term to denote any fungal nail infection. Tinea unguium specifically describes a dermatophytic invasion of the nail plate. Despite the clearly diseased appearance associated with this condition, onychomycosis is all too often regarded as merely a cosmetic problem of relatively minor importance that is hardly worth treating. This belief may have been fostered by the adverse effects and long courses of medication associated with some of the earlier antifungal agents.

However, onychomycosis can have significant negative effects on patients' emotional, social, and occupational functioning. Affected patients may be embarrassed in social and work situations, where they may feel unclean, and are unwilling to permit their hands and feet to be seen. Patients may fear that they will transmit their infection to family members, friends, or coworkers, fears that can lead to diminished self-esteem and avoidance of close relationships. Some patients experience discomfort that prevents them from carrying out tasks such as prolonged standing, writing, or typing.

Onychomycosis in immunocompromised patients, such as those infected with human immunodeficiency virus, can pose a more serious health problem. Not only does this infection serve as a constant reminder to the patient of his or her own deteriorated condition, but the possibility exists of transfer of a very high titer of fungal pathogens to another body site.

The dermatophyte species that most often causes onychomycosis in North America and parts of Europe are *T. rubrum*, *T. metagrophytes*, and *Epidermophyton floccosum*. The first two are much more often implicated than *E. floccosum*. Both dermatophytes and non-dermatophytes, especially *Candida Sp.*, have been identified as etiologic agents of onychomycosis.

Contact with the source of infection constitutes a risk factor. Several factors unique to modern life have resulted in an increased prevalence of onychomycosis, including wearing of shoes, especially tight, high-heeled shoes; the increased use by large numbers of people of damp spaces such as locker rooms and gymnasiums; the declining health of the aging American population, and the increased number of immuno-compromised patients through disease (HIV) or therapeutic agents (immunosuppressive therapies associated with cancer or posttransplantation, and the extensive use of broad-spectrum antibiotics). Other factors that increase the risk of onychomycosis are direct trauma to the nail, including that resulting from certain tic disorders (nail biting).

Treatment of onychomycosis has been attempted for many generations, but success has been limited. Because of the perception that the lesions had a superficial cause, the earliest remedies were topical. However, topical drugs such as the imidazoles, the allylamines, and the pyridone cyclopiroxolamine proved to be generally ineffective against fungal infections of the nails because of their inability to penetrate the entire nail unit and eradicate the infection. Only recently, when the fungal nature of these infections was appreciated, have systemically active drugs been available for treating onychomycosis.

Many currently available antifungal agents require a long duration of therapy, sometimes for over one year, in order to completely treat the onychomycosis. Griseofulvin has limited efficacy because its activity is limited to dermatophytes and a prolonged duration of therapy is required for maximum efficacy. Ketoconazole cannot be used for long-term cure of onychomycosis because of the occurrence of side effects and significant drug interactions. Other previously used drugs include itraconazole, fluconazole, and terbinafine.

Additionally, serious damage is done to crops each year by fungal infections of plants such as smuts, rusts, ergot, and mildews.

Botrytis bunch rot has long been a problem in vineyards. High nitrogen fertilization predisposed grapevines to infection by *Botritis cinerea* and increased disease severity. In vitro results of tests of a number of fungicides were described by R=Houma et al. in *Journal of Plant Pathology* 80(2): 1998, abstracts of papers. Of the fungicides tested, Vinchlozoline, Chlorothalonil, and Dichlofluanide were effective in completely terminating conidia. Iprodione and Procymedone were apparently confronted with the problem of fungal resistance. Folpel, copper and chlorothalonil were not able to control mycelial growth as effectively as conidial germination.

Several *Fusarium* species occurring worldwide on cereals as causal agents of "head blight" of small grain cereals and "ear rot" of corn, can accumulate mycotoxins in infected kernels. Besides being damaging to the cereal crops, some of these mycotoxins are dangerous to animal and/or human health. The main groups of *Fusarium* toxins commonly recognized in grains are trichothecenes: including T-2 toxin (T2), diacetoxyscirpenol, deoxynivalenol, fusarenone X, and nivalenol; zearalenones, primarily zaearalenone; and fumonisins, in particular fumonisin $B_1$. Additionally, moniliformin, beauvericine, and fusaproliferin were also found in *Fusarium* infected cereal ears.

Boronic acids, such as phenylboronic acids, have been known to inhibit acid lipase. This property of phenyl boronic acids has been exploited for disrupting the epithelial barrier function to enhance penetration of topically applied active ingredients, as disclosed in Thronfeldt et al., U.S. Pat. No. 6,190,894.

Boric acid and certain phenyl boronic acids are also inhibitors of certain beta-lactamases. Shoichet et al., in U.S. Pat. Nos. 6,075,014 and 6,184,363, disclose that a number of phenyl boronic acids are effective against bacteria resistant to beta-lactam antibiotics as a result of porin mutations. These compounds, or pharmaceutically acceptable salts, are antibacterial by themselves, although at higher concentrations than beta-lactam antibiotics. It is believed that this antibacterial activity is due to the binding of the inhibitors to penicillin binding proteins (PBPs), which resemble beta-lactamases. Since PBPs are found in all bacterial species susceptible to beta-lactam antibiotics, it is expected that these compounds will be effective against the same bacteria as the beta-lactam antibiotics.

To the best of the present inventors=knowledge, there is no prior art describing any antifungal activity of PBA or its derivatives.

SUMMARY OF THE INVENTION

It is an object of the present invention to overcome the deficiencies in the prior art.

It is another object of the present invention to provide a method for treating onychomycosis.

It is still another object of the present invention to provide methods for treating fungal infections in animals and plants.

It is another object of the present invention to provide a composition which is a substrate for cytochrome p450.

It has now been discovered that phenyl boronic acid and derivatives thereof as well as related boronic acid compounds have fungicidal properties, and that these compounds are particularly useful in treating fungal infections. These compounds have been found to be particularly useful in treating nail fungal infections.

It is known that phenyl boronic acid and derivatives thereof have inhibitory activity toward proteases and lactamases, and it has been reported that it is a substrate for cytochrome p450. (cf. Koehler et al., (1971); Koehler et (1974); Lindquist et al., (1974); and Matthews et al., (1975)).

It is believed that the substrate effect for cytochrome p450, in combination with its water solubility properties, permits phenyl boronic acid or derivatives thereof to enter a cell and to be degraded by cytochrome p450 to a toxic phenyl compound, which then kills the cell. However, this is merely a hypothesis, and the present invention is not bound by this probable mechanism.

BRIEF DESCRIPTION OF THE DRAWINGS

The drawing shows the result of PBA and its derivatives on *T. rubrum*.

DETAILED DESCRIPTION OF THE INVENTION

Figure 1:
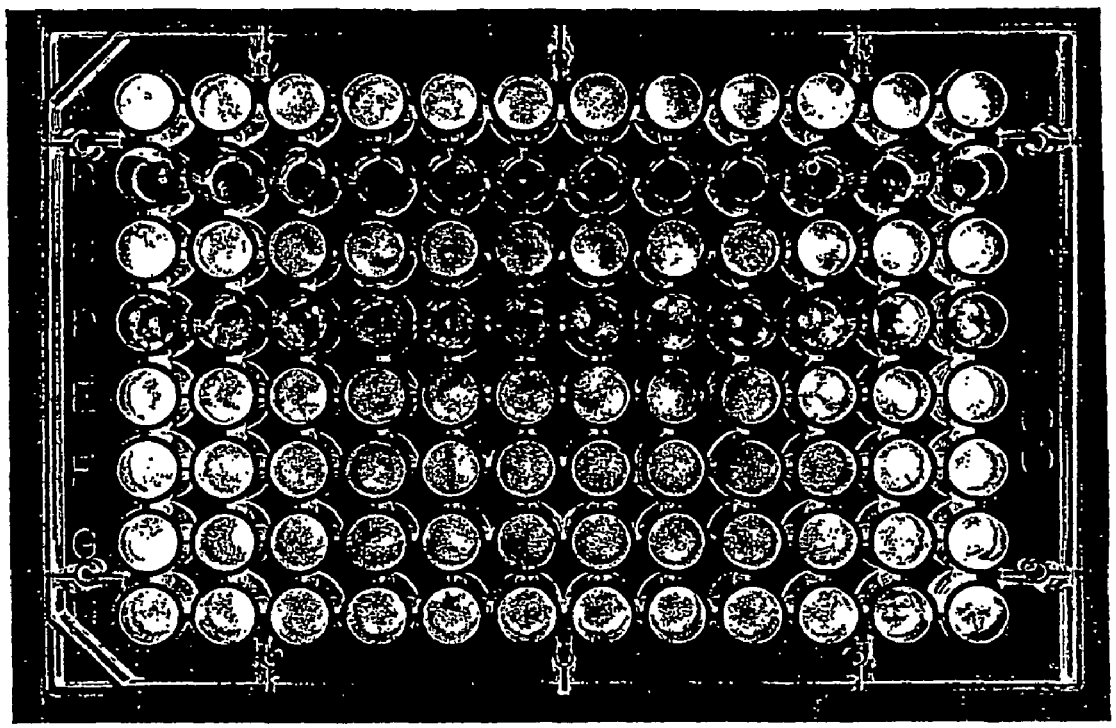

The compounds which are useful for treating fungal infections have the formula

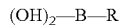  (I)

wherein:
R is substituted or unsubstituted phenyl, naphthalene, phenanthrene, or has one of the following formulas:

  (2)

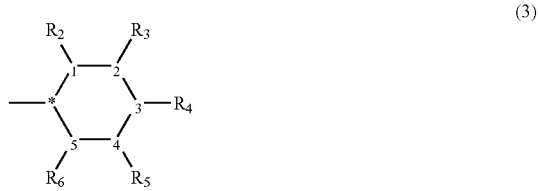  (3)

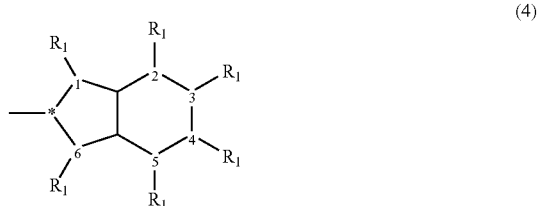  (4)

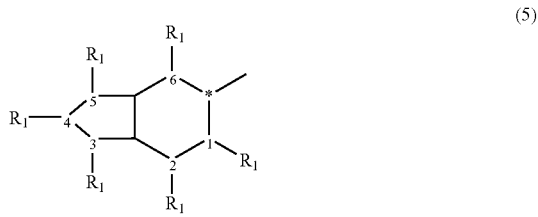  (5)

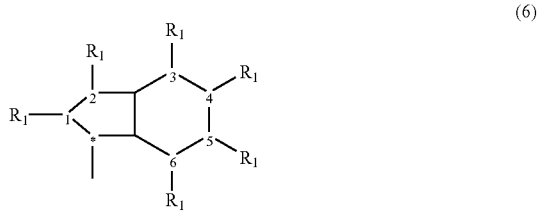  (6)

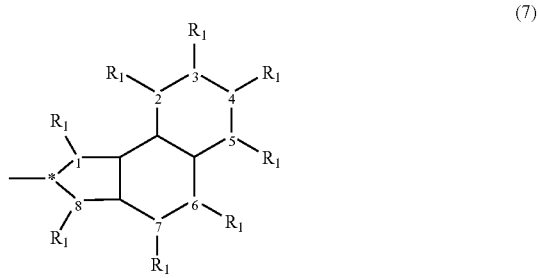  (7)

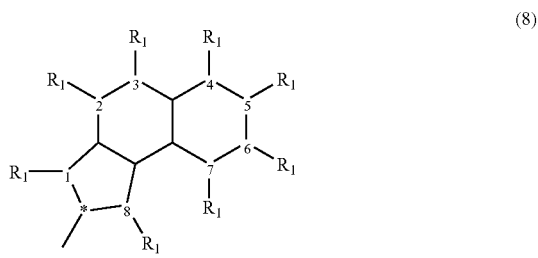  (8)

-continued

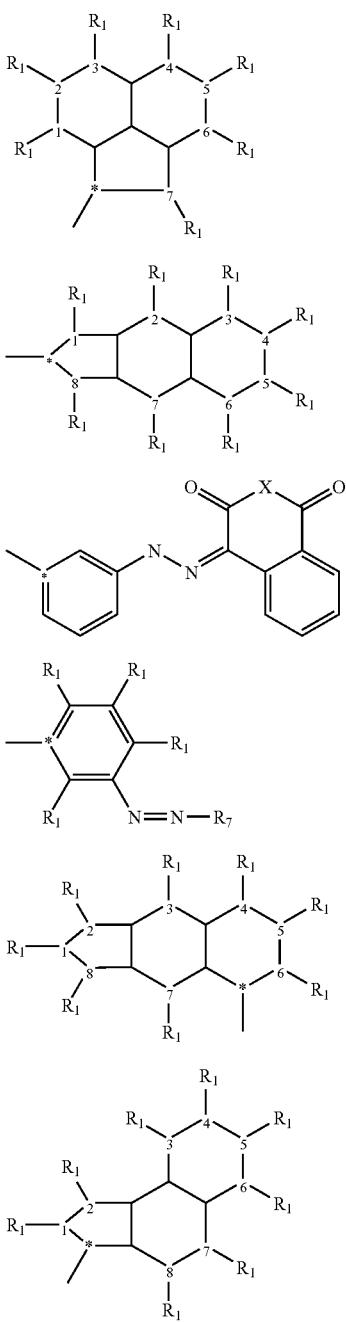

wherein:
ring system (2), (3), (4), (5), (6), (7), (8), (9), (10), (13) or (14) is aromatic or nonaromatic;
the atom center * is (R) or (S) in the case of chiral compounds;
positions 1, 2, 3, 4, 5, 6, 7 and 8 each independently is C, N, O or S;
$R_1$ through $R_6$ each independently is a lone pair, H, $B(OH)_2$, a halogen atom, $CF_3$, $CH_2CF_3$, $CCl_3$, $CH_2CCl_3$, $CBr_3$, $CH_2CBr_3$, $NO_2$, lower alkyl, $CO_2H$, CHCHCOOH, $CH_2CH_2COOH$, $SO_3H$, $PO_3H$, $OSO_3H$, $OPO_3H$, OH, $NH_2$, $CONH_2$, $COCH_3$, $OCH_3$, or phenyl boronic acid.

$R_7$ is H, $CF_3$, $CCl_3$, $CBr_3$, $CH_2CF_3$, $CH_2CCl_3$, $CH_2CBr_3$, $NO_2$, $COCH_3$, $OCH_3$, lower alkyl, cyclic alkene, cyclic alkene substituted with one or more substituents $R_8$, heterocyclic alkene, or heterocyclic alkene substituted with one or more substituent $R_8$;
each $R_8$ is independently H, $B(OH)_2$, a halogen atom, $CF_3$, $CCL_3$, $CBr_3$, $CH_2CF_3$, $CH_2CCl_3$, $CH_2CBr_3$, $NO_2$, lower alkyl, OH, $NH_2$, $N(CH_3)_2$, $N(CH_3)CH_2CH_3$, $NHCOCH_3$, COOH, CHCHCOOH, $CH_2CH_2CH_2COOH$, $COCH_3$, $OCH_3$, phenyl boronic acid, $CONH_2$, $CONHCH_2COOH$, $CONHCH_2CONH_2$, $CONHCH_2CONHCH_2R_{10}$, $SO_2NH_2$, $SO_2NHCH_2COOH$, $SO_2NHCH_2CONH_2$, or $SO_2NHCH_2CONHCH_2R_{10}$;
X is O, NH, $NCH_3$ or

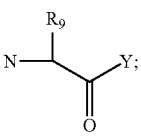

Y is OH, $NH_2$, $NCH_3$, $N(CH_3)_2$, $NHCOCH_3$ or $NHCOCH_2COOH$;
$R_9$ is H, a halogen atom, $CH_3$, $CCl_3$, $CBr_3$, $CH_2CF_3$, $CH_2CCl_3$, $CH_2CBr_3$, $NO_2$, $CO_2H$, CHCHCOOH, $CH_2CH_2CH_2COOH$, $SO_3H$, $PO_3H$, $OSO_3H$, $OPO_3H$, OH, $NH_2$, $CONH_2$, $COCH_3$, $OCH_3$, phenyl boronic acid, lower alkyl, or a side chain of a standard amino acid; and
$R_{10}$ is a side chain of a standard amino acid.

In formula (a) above, the following terms have the following meanings:

"A lone pair" refers to an unshared pair of electrons (not involved in an actual covalent chemical bond to another atom) that may have important interactions in receptor-ligand (e.g., enzyme-inhibitor) complexes.

"Alkyl" means a straight-chain or branched-chain alkyl containing 1-25 carbon atoms.

"Lower alkyl" means a straight-chain or branched-chain alkyl containing 1-4 carbon atoms. Both of these terms include the R and S isomers.

"Cyclic alkene" means a structure containing from 1 to 3 rings, each ring containing from 5 to 6 carbon atoms and at least one double bond. One, two, or all three of the rings may be aromatic.

"Heterocyclic alkene" means a cycle alkene as defined above wherein at least one of the ring(s) contains one or more atoms of S, N, or O.

The "standard amino acids" are alanine, arginine, asparagine, aspartic acid, cysteine, glutamic acid, glutamine, glycine, histidine, homoserine, hydroxyproline, isoleucine, leucine, lysine, methionine, norleucine, norvaline, ornithine, glutamic acid, serine, threonine, tryptophan, tyrosine, and valine. Both the D and L isomers can be used. The side chains of these amino acids are well known and are the portions of the amino acids attached to the $NH_2$—$Ch_2$-COOH backbone. For instance, the side chain of alanine is $CH_3$, and the side chain or asparagine is $CH_2CONH_2$.

The most useful of these compounds for topical antifungal activity are those which are the most water soluble.

Phenyl boronic acid is a commercially available synthetic organic compound which has previously been used for complex formation with diols, sugars, and nucleotides (Singhal et al., *Advances on Chromatography* 31:293-335, Marcel Dekker, NY, 1990) or as a synthetic reagent for Suzuki ether synthesis (Theil, *Angew. Chem., Int. Ed.* 38:2345-2347 1999). Phenyl boronic acid has inhibitory activity towards a series of proteases and lactamases (Philipp et al; *Proceedings of the Natl. Acad. Sci. USA,* 68:1971, (1976). Phenyl boronic acid (PBA) is reasonably soluble in water as well as in several organic solvents. Many of its derivatives are also water soluble. Data on its toxicity are incomplete. PBA is considered harmful if swallowed (ORL-RAT $LD_{50}$: 740 mg/kg).

Additional methods for synthesizing phenyl boronic acids according to the present invention are provided in Shoichet et al., U.S. Pat. No. 6,184,363, the entire contents of which are hereby incorporated.

The water-soluble PBA or derivatives thereof are administered topically in the form of a buffered solution, lotion, or ointment. The compounds are effective over a wide pH range, although a pH of from about 6.0 to about 9.0 is preferred. Generally, the compositions are applied topically once daily until cure.

An in vitro test was designed for testing the fungicidal or fungistatic activity of PBA and its water-soluble derivatives. Cultures of *T. rubrum* were grown on 100 microliters SDB agar in a standard 96 well plate. Following an initial growth period of about 24 hours, each well was treated with 50-100 microliters of the reagent tested. Following an appropriate incubation period with or without washing, residual viability was estimated from comparison with appropriate controls, followed by secondary verification of viability tests by transfer of a part of the treated culture into a fresh well for optional recovery and growth.

The FIGURE shows the results of this assay. The photograph was taken four days after treatment. A photograph taken eight days after treatment was very similar.

The effect of PBA and derivatives on *T. rubrum* as shown in the FIGURE is as follows:
A: control, no treatment
B: 5 mg/ml PBA
C: 5 mg/mk 3-amino PBA
D: 3 mg/ml 3-nitro PBA
E. 5 mg/ml pentafluoro-PBA
F-H: Controls, no treatment It can readily be seen from the above that PBA exhibited fungicidal effects on *T. rubrum* within the concentration range of 5-10 mg/ml tested. These solutions also exhibited a fungistatic effect on *C. parapsylosis* at 5 mg/ml, and a fungicidal effect at 10 mg/ml. Furthermore, a solution of about 5-10 mg/ml had an antibiotic activity against *Bacillus megaterium*.

Three water-soluble derivatives of PBA were also tested. These water soluble derivatives exhibited similar activities.

All of the recorded effects were effective within a wide pH range.

The following table shows the fungicidal and inhibitory effect of PBA and three derivatives thereof, 3-nitro PBA, 3-amino PBA, and pentafluoro PBA at varying concentrations against a variety of bacteria and fungi. It should be noted that none of these compounds was either fungicidal or inhibitory against *Saccharmoyces cerevisiae*. The pharmacologically active compounds of this invention can be processed in accordance with conventional methods of pharmacy to produce medicinal agents for administration to patients, e.g., mammals including human beings. For example, the compounds of formula (I) can be employed in admixtures with conventional excipients, e.g., pharmaceutically acceptable carrier substances suitable for topical application which do not deleteriously react with the active compounds.

|  | PBA (Phenylboronic Acid) | | | 3-NitroPBA | 3-AminoPBA | Pentafluoro PBA |
|---|---|---|---|---|---|---|
|  | 0.04 M | 0.06 M | 0.08 M | 0.03 M | 0.03 M | 0.024 M |
| *Trichophyton rubrum* | F | F | F | F IN (0.02 M) | NE | NE |
| *Candida parapsilosis* | IN | F | F | — | — | — |
| *Saccharomyces cereviasiae* | NE | NE | NE | — | — | — |
| *Butrytis cinerea* (race BO-510) | IN | IN | F | IN | NE | NE |
| *Cochilobolus heterostrophus* (race C4) | IN | F | F | F | NE | NE |
| *Bacilus megaterium* | F | F | F | IN/F | NE | NE |

F = Fungicidal; IN = Inhibitory; NE = No effect
*T. rubrum, C. parapsilosis:* Onychomycosis
*B. cinerea, C. heterostrophus:* Plant pathogens
*S. cerevisiae:* Control (Baker = s yeast)
*B. megaterium:* Control (Cyt P-450 containing bacteria)

Suitable pharmaceutically acceptable carriers include but are not limited to water, salt solutions, alcohols, gum arabic, vegetable oils (e.g., corn oil, cottonseed oil, peanut oil, olive oil, coconut oil), fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring, and/or one or more other active compounds, for example, other antifungal agents, etc.

For treating humans and other animals, the compositions are applied topically. For treating plants, the compositions can be applied, formulated or unformulated, directly to the foliage of a plant, to seeds or to other medium in which plants are growing or are to be planted. They can be sprayed on, dusted on or applied as a cream or paste formulation; or they can be applied as a vapor or as controlled-release granules.

Application can be to any part of the plant including the foliage, stems, branches or roots, or to soil surrounding the roots, or to the seed before it is planted; or to the soil generally, or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate their dispersion in liquids. The powders and granules may also contain fillers and suspending agents.

Suspension concentrates of largely insoluble so lids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g., fluorotrichloromethane or dichlorodifluoromethane.

The invention compounds can be mixed in the dry state with a pyrotechnic mixture to form a composition suitable for generating in enclosed spaces a smoke containing the compounds. Alternatively, the compounds may be used in a microencapsulated form.

They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities. The dosage administered depends upon the age, health, and weight of the recipient, nature of concurrent treatment, if any, and the nature of the effect desired.

Compositions within the scope of the present invention include all compositions wherein the active ingredient is contained in an amount effective to achieve its intended purpose. While individual needs vary, determination of optimal ranges of effective amounts of each compound is within the skill of the art.

Pharmaceutical compositions for administering the active ingredients of the present invention preferably contain, in addition to the pharmacologically active compound, suitable pharmaceutically acceptable carriers comprising excipients and auxiliaries which facilitate processing of the active compounds into preparations which can be used pharmaceutically. Preferably, the preparations, contain from about 0.01 to about 99 percent by weight, preferably from about 20 to 75 percent by weight, active compound(s), together with the excipients. For purposes of the present invention, all percentages are by weight unless otherwise indicated. In addition to the following described pharmaceutical composition, the compounds of the present invention can be formulated as inclusion complexes, such as cyclodextrin inclusion complexes.

The pharmaceutically acceptable carriers include vehicles, adjuvants, excipients, or diluents that are well known to those skilled in the art and which are readily available. It is preferred that the pharmaceutically acceptable carrier be one which is chemically inert to the active compounds and which has no detrimental side effects or toxicity under the conditions of use.

The choice of carrier is determined partly by the particular active ingredient, as well as by the particular method used to administer the composition. Accordingly, there is a wide variety of suitable formulations of the pharmaceutical compositions of the present invention. Generally, formulations are prepared for topical or mucosal administration.

Any number of assays well known in the art may be used to test whether a particular compound suspected of being a fungicide, can be used. These assays are conventional and can be readily adapted to the compounds of the present invention by one skilled in the art without undue experimentation. Examples of assays for fungicidal activity on plants can be found in Wagner et al., U.S. Pat. No. 6,262,091, and Schelberger et al., U.S. Pat. No. 6,258,801, the entire contents of which are hereby incorporated by reference. Examples of assays for fungicidal activity on skin infections can be found in Coury et al., U.S. Pat. No. 6,261,544, the entire contents of which are hereby incorporated by reference.

In determining the dosages of the PBA or derivative thereof to be administered, the dosage and frequency of administration is selected in relation to the pharmacological properties of the specific active ingredients. Normally, at least three dosage levels should be used. In toxicity studies in general, the highest dose should reach a toxic level but be sublethal for most animals in the group. If possible, the lowest dose should induce a biologically demonstrable effect. These studies should be performed in parallel for each compound selected.

When a suitable and presumably safe dosage level has been established as outlined above, studies on the drug=s chronic toxicity, its effect on reproduction, and potential mutagenicity may also be required in order to ensure that the calculated appropriate dosage range will be safe, also with regard to these hazards.

Pharmacological animal studies on pharmacokinetics revealing, e.g., absorption, distribution, biotransformation, and excretion of the active ingredient and metabolites are then performed. Using the results obtained, studies on human pharmacology are then designed. Studies of the pharmacodynamics and pharmacokinetics of the compounds in humans should be performed in healthy subjects using the routes of administration intended for clinical use, and can be repeated in patients. The dose-response relationship when different doses are given, or when several types of conjugates or combinations of conjugates and free compounds are given, should be studied in order to elucidate the dose-response relationship, the therapeutic range, and the optimum dose interval.

The compounds of the present invention are then ready for clinical trials to compare the efficacy of the compounds to existing therapy. A dose-response relationship to therapeutic effect and for side effects can be more finely established at this point.

The amount of compounds of the present invention to be administered to any given patient must be determined empirically, and will differ depending upon the condition of the patients. Relatively small amounts of the active ingredient can be administered at first, with steadily increasing dosages if no adverse effects are noted. Of course, the maximum safe toxicity dosage as determined in routine animal toxicity tests should never be exceeded.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, typically 10-85%, and preferably 25-60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g., compounds having similar or complementary fungicidal activity or which possess plant growth regulating, herbicidal or insecticidal activity, or which can be used in treating skin or nails, including maisturizers, skin softeners, etc. The other fungicide can have a synergistic effect on the fungicidal activity of the compound of the invention. Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, 4-chloro-N-(cyanoethoxymethyl)benzamide, benalaxyl, fosetylaluminium, fenarimol, iprodione, prothiocarb, procymidone, vinclozolin, penconazole, myclobutanil, propamocarb, diconazole, pyrazophos, ethirimol, ditalimfos, tridemorph, triforine, nuarimol, triazbutyl, guazatine, triacetate salt of 1,1'-iminodi(octamethylene)diguanidine, buthiobate, propiconazole, prochloraz, carboxin, oxycarboxin, methfuroxam, dodemorph, BAS 454, blasticidin S, Kasugamycin, edifenphos, kitazin P, cyclohex-imide, phthalide, probenazole, dithianon, fentin hydroxide, fentin acetate, tecnazene, quintozene, dichloran, copper containing compounds such as copper oxychloride, copper sulphate and Bordeaux mixture, and organomercury compounds. The compounds of the invention can be mixed with soil, peat or other rooting media for the protection of plants against seed-borne, soil-borne or foliar fungal diseases.

Derivatives of phenyl boronic acid include, for example, compounds having the following formula:

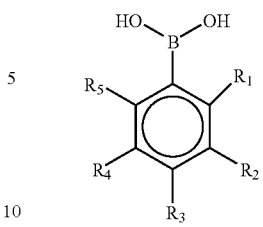

wherein $R_1$, $R_2$, $R_3$, $R_4$, and $R_5$ are individually selected from the group consisting of hydrogen, fluoro, chloro, bromo, nitro, amino, methanesulfonyl, methoxycarbonyl, substituted or unsubstituted lower alkyl ($C_1$-$C_6$ carbon atoms), substituted or unsubstituted lower alkoxy ($C_1$-$C_6$ carbon atoms), substituted or unsubstituted aryl ($C_6$-$C_{12}$ carbon atoms), substituted or unsubstituted aryloxy ($C_6$-$C_{12}$ carbon atoms), cyano, or cycloalkyl.

Nonlimiting examples of phenyl boronic acids that can be used in the present invention include 2,6-dichlorophenylboronic acid, 2-(4-dihydroxyborane)phenyl carboxylquinoline, 4-(methanesulfonyl)phenyl boronic acid; 4-methoxycarbonylphenyl boronic acid, 4-phenoxyphenylboronic acid, 3-acetylphenylboronic acid; benzothiophene-2-boronic acid, biphenyl-3-boronic acid, 2,4, bis(benzyloxy)pyrimidine-5-boronic acid, 1,5, bis(hexyl)1,4-benzenebis(boronic acid), 4-bromomethylphenylboronic acid, 4-bromophenylboronic acid, 4-bromophenylboronic acid, 1-(t-butoxycarbonyl)pyrrole-2-boronic acid, 3-carboxyphenylboronic acid, 4-carboxyphenylboronic acid, 5-chloro-2-methoxyphenylboronic acid, 2-chlorophenylboronic acid, 3-chlorophenylboronic acid, 4-chlorophenylboronic acid, 5-chlorothiophene-2-boronic acid, 3-cyanophenylboronic acid, 4-cyanophenylboronic acid, 2,5,-dichlorophenylboronic acid, 2,4-difluorobenzeneboronic acid, 2,6-difluorophenylboronic acid, 2,4-dimethloxybenzeneboronic acid, 2,5-dimethoxyphenylboronic acid, 2,6-dimethoxyphenylboronic acid, 3,4-dimethoxyphenylboronic acid, 2,4-dimethoxypyrimidine-5-boronic acid, 2-fluorophenylboronic acid, 4-fluorophenylboronic acid, 2-formylphenylboronic acid, 3-formylphenylboronic acid, 4-formylphenylboronic acid, 4-iodophenylboronic acid, 4-methoxycarbonylphenylboronic acid, 2-methoxy-5-formylphenylboronic acid, 4-methoxy-2-formylphenylboronic acid, 5-methoxy-2-formylphenylboronic acid, 2-methoxyphenylboronic acid, 3-methoxyphenylboronic acid, 4-methoxyphenylboronic acid, 2-methoxy-5-pyridineboronic acid, 2-methoxy-5-pyridineboronic acid dimethyl ester, 3,4-methylenedioxyphenylboronic acid, 4-(methanesulfonyl)phenylboronic acid, 4-methylthiophene-2-boronic acid, 5-methylthiophene-2-boronic acid, naphthalene-1-boronic acid, naphthalene-2-boronic acid 97+%, phenoxathiin-4-boronic acid, 4-phenoxyphenylboronic acid, phenylboronic acid, pyridine-3-boronic acid, 8-quinoline boronic acid, thianthrene-1-boronic acid, 4-thioanisoleboronic acid, thiophene-2-boronic acid, thiophene-3-boronic acid, 2-tolylboronic acid 97%, 3-tolylboronic acid, 4-tolylboronic acid 97%, 2,4,6-trichlorophenylboronic acid, 2-trifluoromethylphenylboronic acid, 3-trifluoromethylphenylboronic acid, 4-trifluoromethylphenylboronic acid, 4-(trimethylammonium)methylphenylboronic acid bromide salt, and 2,4,6-trimethylphenylboronic acid.

For treating human fungal infections, the phenylboronic acid derivative or related compound will be dispersed in a cosmetic or therapeutic vehicle. For example, topical cosmetic compositions include an effective amount of the active compound and a cosmetic agent in a cosmetically acceptable vehicle. When applied to the skin or nails, the requisite amounts of PBA compound will depend on the type of application, the duration desired for the effect, and on any compensation required for penetration into the upper layers of the skin, or the degree of abrasion and shedding of the skin. The PBA compound will be present in the overall formulation in amounts ranging rom about 0.1% to about 100% by weight, depending upon the use of the formulation. In most uses, ranges from about 1% to about 80% are preferred, and ranges from about 2% to about 50% are most preferred. Preferably, the pH of the formulation when applied to the skin or nails is in the range of about 4.0 to about 9.0 so as to reduce irritation to the infected skin or nails.

A pharmaceutically or cosmetically acceptable vehicle can include a powder, lotion, gel, spray, stick, cream, ointment, liquid, emulsion, foam or aerosol. The active PBA compound can be incorporated into a liquid in dissolved form or colloidal form. The liquid can be a solvent, partial solvent, or non-solvent. Since the active PBA compounds are water-soluble, water is a preferred solvent.

Alternatively, the PBA compound can be applied as a powder. It can be applied as a dry powder to moist skin or mails, or as a premoistened powder to dry skin or nails. Preferably, the resultant paste or solution is allowed to dry to form an essentially invisible skin or nail coating.

The compositions can include any solid, semi-solid or liquid cosmetically and/or pharmaceutically acceptable vehicle to enable the active ingredient to be conveyed to the affected skin or nail area at an appropriate dilution. The nature of the vehicle will depend upon the method chosen for topical administration of the composition. The vehicle itself can be inert, or it can possess physiological or pharmaceutical benefits of its own. The selection of a vehicle depends on the required product form of the composition.

Examples of cosmetic agents include emollients, humectants, colorants, pigments, fragrances, moisturizers, viscosity modifiers, and any other conventional cosmetic forming agent. One or more cosmetic agents can be included in the cosmetic composition. The form of the cosmetic composition can be a powder, lotion, gel, spray, stick, cream, ointment, liquid, emulsion, foam or aerosol. Lists of such materials, and formulations for the creation of particular types of lotions, creams, sunscreens, lipsticks, and other such forms are widely available in the patent literature and in commercial handbooks, and can be used by those skilled in the preparation of such formations to incorporate the active ingredient.

Additional additives that can be included in the formulations are described in Coury et al., U.S. Pat. No. 6,261,544, the entire contents of which are hereby incorporated by reference.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

REFERENCES

Koehler et al., *Biochemistry* 10(13):2477-2483 (1971)
Koehler et al., *Biochemistry* 13(26):5345-5350 (1974)
Lindquist et al., *Archives of Biochemistry and Biophysics* 160:135-144 (1974)
Matthews et al., the *Journal of Biological Chemistry* 250(18): 7120-7126 (1975)

What is claimed is:

1. A method for treating onychomycosis comprising topically administering to an animal afflicted with onychomycosis a fungicidally effective amount of phenylboronic acid or a water soluble derivative thereof, said water soluble derivative having substantially similar or better antifungal properties for animals as phenylboronic acid.

2. The method according to claim 1, wherein the fungal infection results from infection with a fungus selected from the group consisting of *T. rubrum, T. metagrophytes, C. parapsilosis*, and *E. floccosum*.

3. The method according to claim 1, wherein the phenylboronic acid or derivative thereof is selected from the group consisting of compounds of the formula:

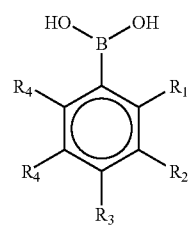

wherein $R_1$, $R_2$, $R_3$, $R_4$, and $R_5$ are individually selected from the group consisting of hydrogen, halogen, amino, methanesulfonyl, methoxycarbonyl, substituted or unsubstituted lower alkyl ($C_1$-$C_6$ carbon atoms), substituted or unsubstituted lower alkoxy ($C_1$-$C_6$ carbon atoms), substituted or unsubstituted aryl ($C_6$-$C_{12}$ carbon atoms), substituted or unsubstituted aryloxy ($C_6$-$C_{12}$ carbon atoms), cyano, cycloalkyl, substituted or unsubstituted carboxy sulfate, phosphate, phosphite and hydroxy.

4. A method for treating onychomycosis in an animal comprising topically administering to an animal afflicted with onychomychosis a fungicidally effective amount of a compound selected from the group consisting of compounds of the formula:

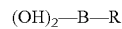

wherein:

R is substituted or unsubstituted phenyl, naphthalene, or phenanthrene, or has one of the following formulas:

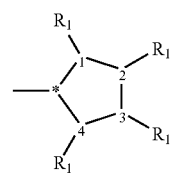

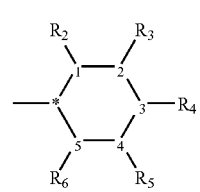

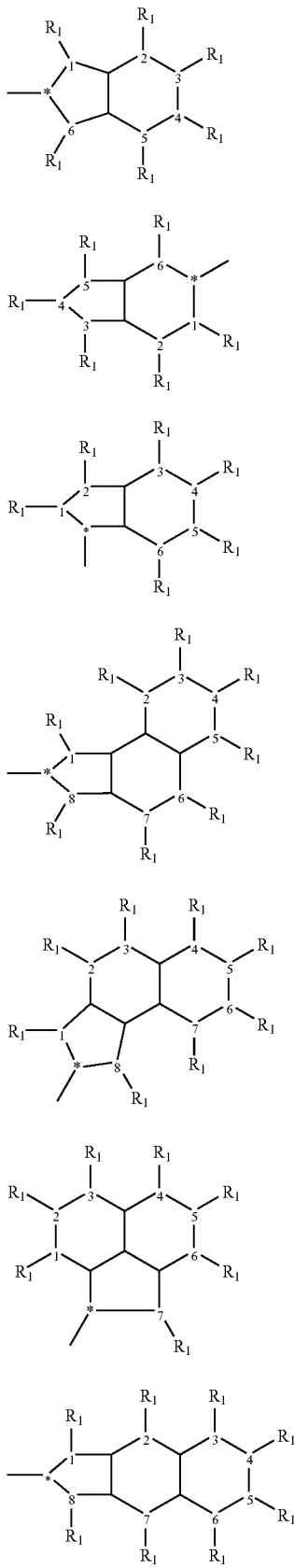
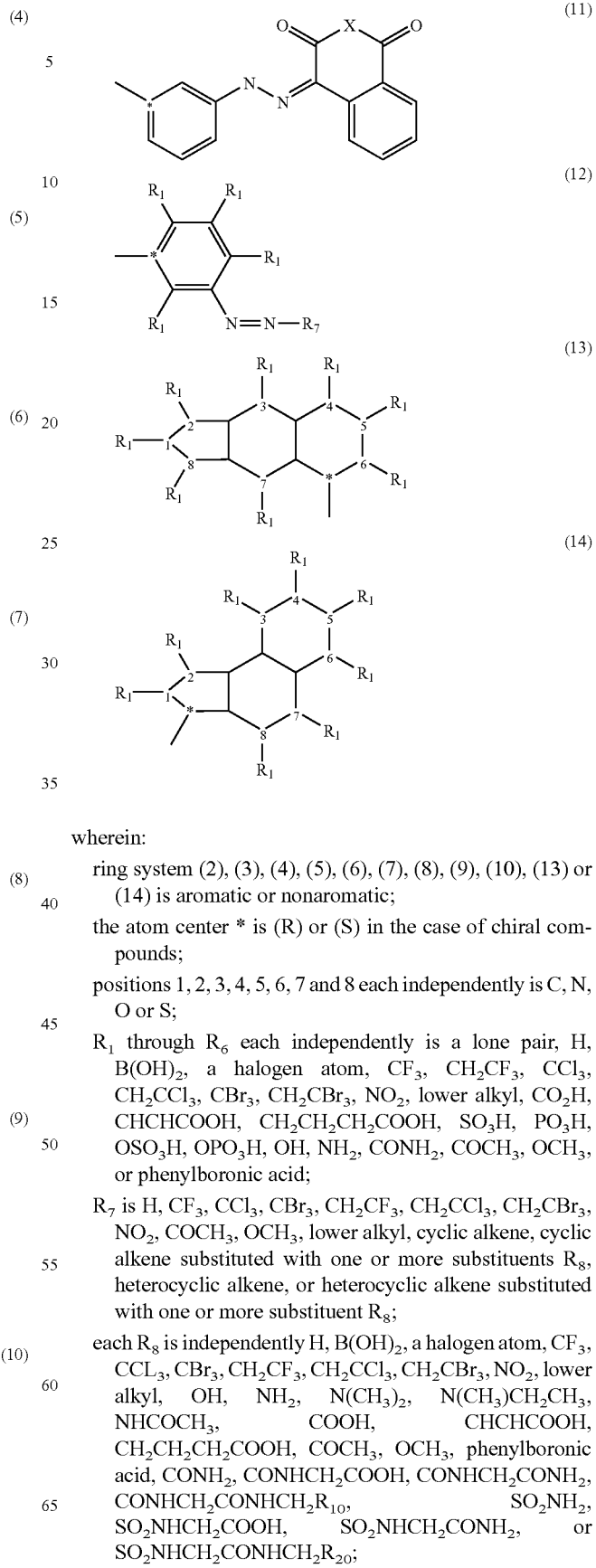

wherein:

ring system (2), (3), (4), (5), (6), (7), (8), (9), (10), (13) or (14) is aromatic or nonaromatic;

the atom center * is (R) or (S) in the case of chiral compounds;

positions 1, 2, 3, 4, 5, 6, 7 and 8 each independently is C, N, O or S;

$R_1$ through $R_6$ each independently is a lone pair, H, $B(OH)_2$, a halogen atom, $CF_3$, $CH_2CF_3$, $CCl_3$, $CH_2CCl_3$, $CBr_3$, $CH_2CBr_3$, $NO_2$, lower alkyl, $CO_2H$, CHCHCOOH, $CH_2CH_2CH_2COOH$, $SO_3H$, $PO_3H$, $OSO_3H$, $OPO_3H$, OH, $NH_2$, $CONH_2$, $COCH_3$, $OCH_3$, or phenylboronic acid;

$R_7$ is H, $CF_3$, $CCl_3$, $CBr_3$, $CH_2CF_3$, $CH_2CCl_3$, $CH_2CBr_3$, $NO_2$, $COCH_3$, $OCH_3$, lower alkyl, cyclic alkene, cyclic alkene substituted with one or more substituents $R_8$, heterocyclic alkene, or heterocyclic alkene substituted with one or more substituent $R_8$;

each $R_8$ is independently H, $B(OH)_2$, a halogen atom, $CF_3$, $CCL_3$, $CBr_3$, $CH_2CF_3$, $CH_2CCl_3$, $CH_2CBr_3$, $NO_2$, lower alkyl, OH, $NH_2$, $N(CH_3)_2$, $N(CH_3)CH_2CH_3$, $NHCOCH_3$, COOH, CHCHCOOH, $CH_2CH_2CH_2COOH$, $COCH_3$, $OCH_3$, phenylboronic acid, $CONH_2$, $CONHCH_2COOH$, $CONHCH_2CONH_2$, $CONHCH_2CONHCH_2R_{10}$, $SO_2NH_2$, $SO_2NHCH_2COOH$, $SO_2NHCH_2CONH_2$, or $SO_2NHCH_2CONHCH_2R_{20}$;

X is O, NH, NCH₃ or

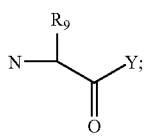

Y is OH, NH₂, NCH₃, N(CH₃)₂, NHCOCH₃ or NHCOCH₂COOH;

R₉ is H, a halogen atom, CH₃, CCl₃, CBr₃, CH₂CF₃, CH₂CCl₃, CH₂CBr₃, NO₂, CO₂H, CHCHCOOH, CH₂CH₂CH₂COOH, SO₃H, PO₃H, OSO₃H, OPO₃H, OH, NH₂, CONH₂, COCH₃, OCH₃, phenylboronic acid, lower alkyl, or a side chain of a standard amino acid; and R₁₀ is a side chain of a standard amino acid.

5. The method according to claim 3, wherein R₁, R₂, R₃, R₄, and R₅, are individually selected from the group consisting of hydrogen, fluoro, chloro, bromo, iodo, acetyl, and methoxy.

6. The method according to claim 5, wherein the compound is 3-chloro-4-fluoro phenylboronic acid.

7. The method according to claim 1, wherein the phenylboronic acid or derivative thereof is a phenylboronic acid derivative selected from the group consisting of 2-formyl phenylboronic acid, 2-acetyl phenylboronic acid, 4-vinyl phenylboronic acid, 3-nitrophenylboronic acid, 3-aminophenylboronic acid, and pentafluorophenylboronic acid.

8. The method according to claim 7, wherein said phenylboronic derivative is 2-formyl phenylboronic acid.

9. The method according to claim 4, wherein the compound is selected from the group consisting of 3-nitrophenylboronic acid, 3-aminophenylboronic acid, and pentafluorophenylboronic acid.

10. A method for treating fungal infections comprising administering to an animal or plant afflicted with a fungal infection an effective amount of a phenylboronic acid derivative selected from the group consisting of 2-formyl phenylboronic acid, 2-acetyl phenylboronic acid, 4-vinyl phenylboronic acid, 3-nitrophenylboronic acid, 3-aminophenylboronic acid, and pentafluorophenylboronic acid.

11. The method according to claim 7, wherein the derivative of phenylboronic acid is 3-aminophenylboronic acid.

12. The method according to claim 7, wherein the derivative of phenylboronic acid is pentafluorophenylboronic acid.

13. The method according to claim 7, wherein the derivative of phenylboronic acid is 2-acetyl phenylboronic acid.

14. The method according to claim 7, wherein the derivative of phenylboronic acid is 4-vinyl phenylboronic acid.

15. The method according to claim 7, wherein the derivative of phenylboronic acid is 3-nitrophenylboronic acid.

16. The method according to claim 10, wherein the derivative of phenylboronic acid is 2-formyl phenylboronic acid.

17. The method according to claim 10, wherein the derivative of phenylboronic acid is 3-aminophenylboronic acid.

18. The method according to claim 10, wherein the derivative of phenylboronic acid is pentafluorophenylboronic acid.

19. The method according to claim 10, wherein the derivative of phenylboronic acid is 2-acetyl phenylboronic acid.

20. The method according to claim 10, wherein the derivative of phenylboronic acid is 4-vinyl phenylboronic acid.

21. The method according to claim 10, wherein the derivative of phenylboronic acid is 3-nitrophenylboronic acid.

* * * * *